United States Patent [19]

Sarnoff

[11] Patent Number: 4,795,433

[45] Date of Patent: Jan. 3, 1989

[54] AUTOMATIC INJECTOR FOR EMERGENCY TREATMENT

[75] Inventor: Stanley J. Sarnoff, Bethesda, Md.

[73] Assignee: Survival Technology, Inc., Bethesda, Md.

[21] Appl. No.: 176,224

[22] Filed: Mar. 31, 1988

Related U.S. Application Data

[60] Division of Ser. No. 735,311, May 20, 1985, and a continuation-in-part of Ser. No. 638,695, Jul. 19, 1984, Pat. No. 4,658,830, and a continuation-in-part of Ser. No. 708,845, Mar. 6, 1985, Pat. No. 4,661,469.

[51] Int. Cl.$^4$ .............................................. A61M 5/20
[52] U.S. Cl. .................................... 604/134; 604/136; 604/187
[58] Field of Search ............................ 604/134–139, 604/181, 187, 82–90

[56] References Cited

U.S. PATENT DOCUMENTS

| | | |
|---|---|---|
| 2,771,554 | 11/1956 | Gratzl . |
| 3,078,850 | 2/1963 | Schein . |
| 3,364,929 | 1/1968 | Ide . |
| 3,380,449 | 4/1968 | Sarnoff . |
| 3,391,695 | 7/1968 | Sarnoff . |
| 3,424,155 | 1/1969 | Sarnoff . |
| 3,565,080 | 2/1971 | Ide . |
| 3,807,411 | 4/1974 | Harris . |
| 3,882,863 | 5/1975 | Sarnoff . |
| 4,031,893 | 6/1977 | Kaplan . |
| 4,103,690 | 8/1978 | Harris . |
| 4,226,235 | 10/1980 | Sarnoff . |
| 4,394,863 | 7/1983 | Bartner . |
| 4,656,034 | 4/1987 | Sarnoff . |
| 4,658,830 | 4/1987 | Sarnoff . |
| 4,661,469 | 4/1987 | Sarnoff . |

OTHER PUBLICATIONS

Iizuka, et al.–Chem. Abst., vol. 77 (1972) p. 17315u.
Korninger et al.–Chem. Abst., vol. 95 (1981) p. 197233u.
Belousov, et al.–Chem. Abst., vol. 92 (1980) p. 39285w.

Lawrence K. Altman, *The New York Times*, "Protein of Cancer Cells Used to Halt Coronaries", Nov. 16, 1983.
Eugene G. Levin, *Proc. Natl. Acad. Sci. USA*, "Latent Tissue Plasminogen Activator Produced by Human Endothelial Cells in Culture: Evidence for an Enzyme–Inhibitor Complex", Nov. 1983, vol. 80, pp. 6804–6808.
Frans van de Werf, et al., *The New England Journal of Medicine*, "Coronary Thrombolysis with Tissue-Type Plasminogen Activator in Patients with Evolving Myocardial Infarction", Mar. 8, 1984, vol. 310, No. 10, pp. 609–613.
Keith A. A. Fox, et al., *Biochemical Pharmacology*, Commentary, "Coronary Thrombolysis: Pharmacological Considerations with Emphasis on Tissue-Type Plasminogen Activator" (t-PA), 1984, vol. 33, No. 12, pp. 1831–1838.

*Primary Examiner*—John D. Yasko
*Attorney, Agent, or Firm*—Cushman, Darby & Cushman

[57] ABSTRACT

A method of treating a patient with liquid medicament under circumstances where intravenous injection is not practical but the fast response time of an intravenous injection is desirable, including the treatment of individuals undergoing heart attack symptoms with t-PA. The method comprises the steps of injecting the liquid medicament t-PA preferably with a blood absorption enhancing agent such as hydroxylamine hydrochloride into the muscle tissue of the patient, applying to the patient which has received the injection repeated blood flow stimulating cycles, each of which includes a period of electrical stimulus during which the muscle tissue which has received the injection tenses followed by a period of no electrical stimulus during which the muscle tissue which received the injection is allowed to relax inducing enhanced blood flow within the muscle tissue, and continuing the application of the repeated blood flow stimulating cycles until the injected liquid medicament has been sufficiently absorbed into the enhanced blood flow to achieve a desired possible patient response of reperfusion and apparatus for carrying out the method.

39 Claims, 3 Drawing Sheets

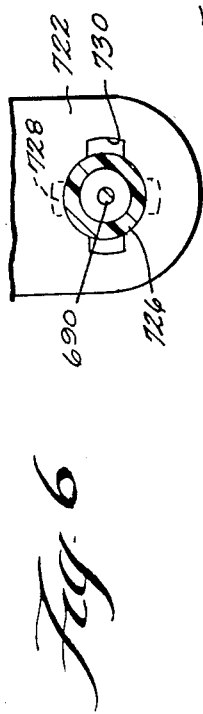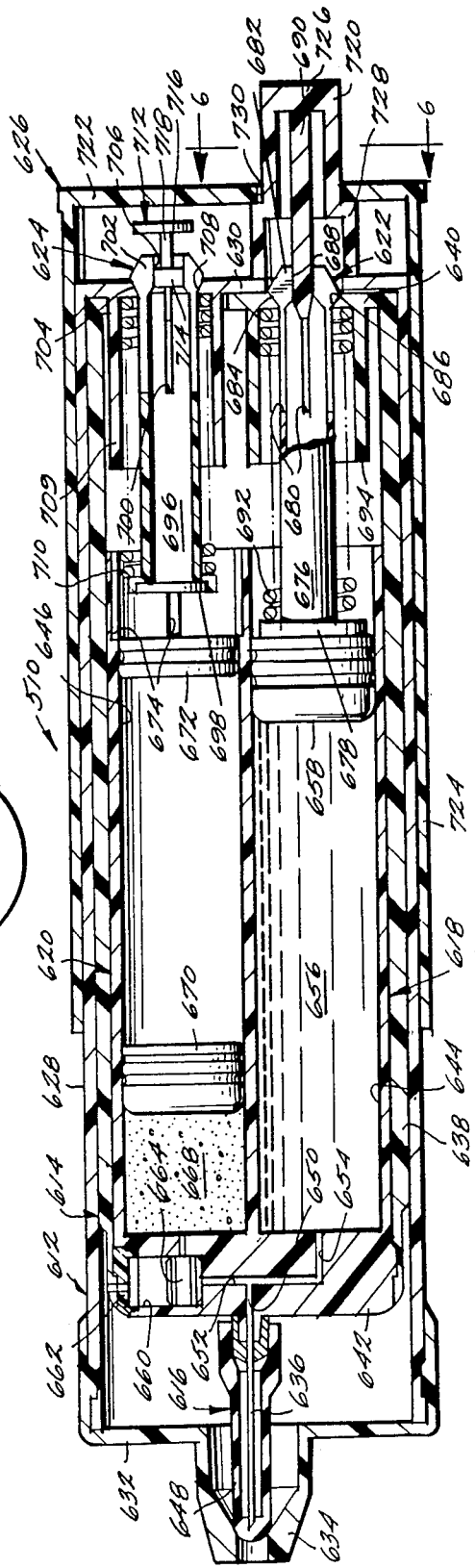

AUTOMATIC INJECTOR FOR EMERGENCY TREATMENT

BACKGROUND OF THE INVENTION

This application is a division of my copending patent application Ser. No. 735,311 filed May 20, 1985, entitled Injection Method and Apparatus with Electrical Blood Absorbing Stimulation, a continuation-in-part of my copending patent application Ser. No. 638,695 filed July 19, 1984 entitled Method and Apparatus for Initiating Reperfusion Treatment by an Unattended Individual Undergoing Heart Attack Symptoms, now U.S. Pat. No. 4,658,830, and a continuation-in-part of my copending patent application Ser. No. 708,845 filed Mar. 6, 1985 entitled t-PA Composition Capable of Being Absorbed into the Blood, now U.S. Pat. No 4,661,469.

This invention relates to the treatment of patients by medicament injection and more particularly to medicament injection treatment under circumstances where intravenous injection is not practical but the fast response time of an intravenous injection is desirable.

One set of circumstances where these conditions are presented is in initiating reperfusion treatment by an unattended individual undergoing heart attack symptoms.

When a clot forms in a blood vessel, the body organ being supplied with blood by that blood vessel is compromised or totally deprived of blood supply. Depending on the blood vessel in which this occurs, the threat to the life of the individual is either small or very great as in the circumstances to be addressed by the material below, i.e. certain life threatening circumstances. Clot formation in a vessel is described as thrombosis. Substances which dissolve thrombi are called thrombolytic substances. When a coronary artery clot is dissolved, the resultant establishment of blood flow to the heart is called reperfusion.

Examples of life threatening clot formation in arterial vessels are cerebral thrombosis, renal thrombosis, ophthalmic artery thrombosis, and very importantly, thrombosis of a coronary artery. In approximately 85% to 90% of cases of acute myocardial infarction (coronary heart attack), a thrombus is found in the coronary artery preventing blood from flowing to the heart muscle (myocardium) and supplying it with essential oxygen and other nutrients. A consequence of a thrombus or clot forming in a coronary artery is the danger to the myocardium (heart muscle tissue that does the pumping of blood). Heart muscle deprived of its blood supply does not die immediately but does begin the process of becoming dead. The extent of the damage which is done to the heart muscle is, therefore, a function of the time during which the supply of blood to the infarct zone is restricted by the clot or occlusion.

Heretofore, the procedures undertaken to actually establish reperfusion to the infarct zone have always been undertaken in a hospital environment or equivalent. The so-called "pre-hospital" treatment was, in general, directed toward keeping the patient alive and getting the patient into the hospital environment as soon as possible so that treatment minimizing the heart muscle damage could be accomplished.

The treatment undertaken in the hospital environment involves certain procedures for establishing reperfusion in the infarct zone of the patient's heart. Where immediate surgery was not clearly indicated, the establishment of reperfusion was accomplished by procedures which had the effect of unblocking the occlusion. The available procedures included mechanical catheterization and the administration of thrombolytic agents. Known thrombolytic agents, such as streptokinase or urokinase required intercoronary infusion or the slow infeed of the agent within the vessel at the site of occlusion by means of a catheter. In recent years, intravenous infusion of streptokinase has been shown to be effective.

More recently a substance called tissuetype plasminogen activator or t-PA has been utilized experimentally. (*The New England Journal Of Medicine*, Mar. 8, 1984, Vol. 310, No. 10, pp. 609–613) Unlike other plasminogen activators, such as streptokinase or urokinase, t-PA—which is found in only small amounts in the body—acts specifically on clots and not on other proteins in the blood, when maintained at appropriate and effective levels.

A 1984 Commentary found in *Biochemical Pharmacology* Vol. 33, No. 12, pp. 1831–1838 entitled "Coronary Thrombolysis: Pharmacological Considerations with Emphasis on Tissue-Type Plasminogen Activator (t-PA)" contains the following conclusionary statement:

"Selection of pharmacological agents for induction of coronary thrombolysis has been determined largely by availability. Unfortunately, both streptokinase and urokinase induce a systemic lytic state with depletion of circulating fibrinogen plasminogen, and $_2$- antiplasmin, and accumulation of fibrin degradation products. All of these factors conspire to set the stage for hemorrhage with a risk of serious bleeding. Intravenous administration of these agents is limited by a lower success rate, in part because the upper bound of dose is constrained by the risk of inducing a severe systemic lytic state.

The probability that progress in recombinant DNA technology will lead to widespread availability of tissue-type plasminogen activator is particularly exciting because of the clot specific properties of t-PA. For coronary thrombolysis its potential advantages include: safety and efficacy of intravenous administration of high doses; effective clot lysis without induction of a systemic lytic state; prompt implementation without the need for extensive characterization of the coagulation and fibrinolytic systems in each patient prior to and during therapy; avoidance of frank allergic reactions or variations in dose-response relation due to immune complex formation; ease of minute-by-minute adjustment of dosage and prompt termination of fibrinolysis when needed because of the short biological half-life of t-PA and the lack of induction of a systemic lytic state."

The promise attributable to t-PA administration was discussed at a news conference at a meeting of the American Heart Association and reported by the New York *Times* on Nov. 16, 1983, in an article entitled, "Protein of Cancer Cells Used to Halt Coronaries." The article refers to injection of t-PA by stating the following: "The protein [t-PA]can simply be injected into the vein in the arm of the patient seized by a myocardial infarction or heart attack, and it travels through the blood to dissolve a clot, in much the same way as Draino clears up stopped plumbing."

The article further indicated under the sub-heading "Hopes for Future Application" that many physicians have expressed excitement about research into the use of t-PA to treat heart attacks because they hope that some day it may be used in emergency rooms and ambulances to stop heart attacks at their earliest stages before they kill or cause permanent damage. Under the "Hopes for Future Application" sub-heading there is also included the following paragraph: "Dr. Burton E. Sobel of Washington University, one of the researchers, speculated that patients might some day carry a vial with them so that the drug could be injected immediately after they felt chest pain and other early symptoms of a heart attack."

In medical parlance, a vial is a container for a quantity of liquid medicine or diluent having a rubber stopper capable of being pierced by a hypodermic needle of a syringe to enable the operator of the syringe to withdraw a predetermined dosage of the liquid from the vial. In the case of t-PA, the dosage could then be injected into the mother liquid container of an infusion assembly. The necessity to administer the drug by slow intravenous infusion or by slow intravenous injection presents a significant barrier to self-administration from a practical view point, particularly when considering the disconcerting circumstances of the individual undergoing the symptoms of a myocardial infaction.

The development of a effective self-administration procedure for t-PA sufficient to enable its utilization by a targeted coronary prone individual immediately following onset of symptoms, would materially increase the potential efficacy of t-PA as a thrombolytic agent by insuring its use at the earliest possible time often before irreversible heart muscle damage has occurred, and, at the same time, provide a treatment of the pre-hospital or pre-ambulance type which for the first time is directly effective to minimize heart muscle damage accompanying myocardial infarction.

With respect to t-PA, a severe threshold question is presented as to whether an intravenous injection would be effective. Even though t-PA may be regarded as a clot selective thrombolytic agent, when introduced into the blood stream at a predetermined level, tests thus far performed show that the concentration can be increased to the point that a systemic lytic state can be induced. Intramuscular injection involves the introduction of a concentrated dosage of t-PA in an area contiguous to and substantially surrounding the wound caused by the penetration and withdrawal of the injection of the hypodermic needle. Consequently, it would be expected that at least a localized lytic state would be induced resulting in hemorrhage from the needle wound. Unexpectedly, tests have shown that no such hemorrhage does in fact occur.

Beyond this threshold question, exists the question of whether sufficient quantities of the t-PA injected into the muscle tissue would be absorbed in time to be effective. t-PA is a large protein. It would not be exected that it would be absorbed into the blood stream in discernible quantities. Extra-vascular levels of protein are about 1/10 that of intravascular protein. It is thought that this is so because the capillary pores through which transport of protein can occur are small relative to the molecular size of protein and limit protein transport because of electrical charge. It was thus highly problematical as to whether a large protein such as t-PA, when given intramuscularly, i.e. outside the blood vessels, would find its way rapidly into the blood stream in discernible quantities. Applicant tests have shown that unexpectedly t-PA does find its way rapidly into the blood stream in discernible quantities after intramuscular injection.

In accordance with the principles of the present invention, enhancement of blood absorption of t-PA may be accomplished in two ways. First, by injecting a blood absorption enhancing agent, such as hydroxylamine hydrochloride, into the muscle tissue along with the t-PA and second, by applying blood absorption enhancing electrical stimulating cycles. Moreover, in order to provide for total treatment it is within the contemplation of the present invention to also inject into the muscle tissue with the t-PA a anti-arrhythmic agent, such as lidocaine, an anti-reclotting agent, which may be either a thromboxane synthetase inhibitor, such as dazoxiben, or an antagonist for the receptor of thromboxane A, such as SQ 27,427 and a reperfusion damage preventing agent, such as superoxide dismutase (SOD) or S-aminotrimethyleneaminoethyl thiophosphate.

In accordance with the principles of the present invention this objective is accomplished by injecting a dosage of the liquid medicament into the muscle tissue of the patient and applying to the patient who has received the injection repeated blood flow stimulating cycles, each of which includes a period of electrical stimulus during which the muscle tissue which received the liquid medicament tenses followed by a period of no electrical stimulus during which the muscle tissue which received the liquid medicament is allowed to relax inducing enhanced blood flow within the muscle tissue and continuing the application of the repeated blood flow stimulating cycles until the injected medicament has been sufficiently absorbed into the blood to achieve patient response.

An object of the present invention is the provision of apparatus for effecting the aforesaid treatment method. Preferably, the injecting means of the apparatus constitutes an automatic injector of the type including a stressed spring releasable by a releasing mechanism actuated in response to the accomplishment of a predetermined muscle actuating procedure. Preferably, the electrical blood flow enhancing cycle applying means includes a pair of electrode elements capable of being operatively applied to the patient through which an electrical circuit is completed so as to directly stimulate the muscle tissue receiving the injection or to stimulate the nerves controlling the muscle tissue receiving the injection so that the aforesaid blood flow stimulating cycles can be repeated.

Another object of the present invention is the provision of an apparatus of the type described which is simple in construction, effective in operation and economical to manufacture.

These and other objects of the present invention will become more apparent during the course of the following detailed description and appended claims.

The invention may best be understood with reference to the accompanying drawings wherein illustrative embodiments are shown.

In the drawings:

FIG. 5 is a sectional view of the automatic injector shown in FIG. 1; and

FIG. 6 is a sectional view taken along the line 6—6 of FIG. 5.

Figures 1, 2:
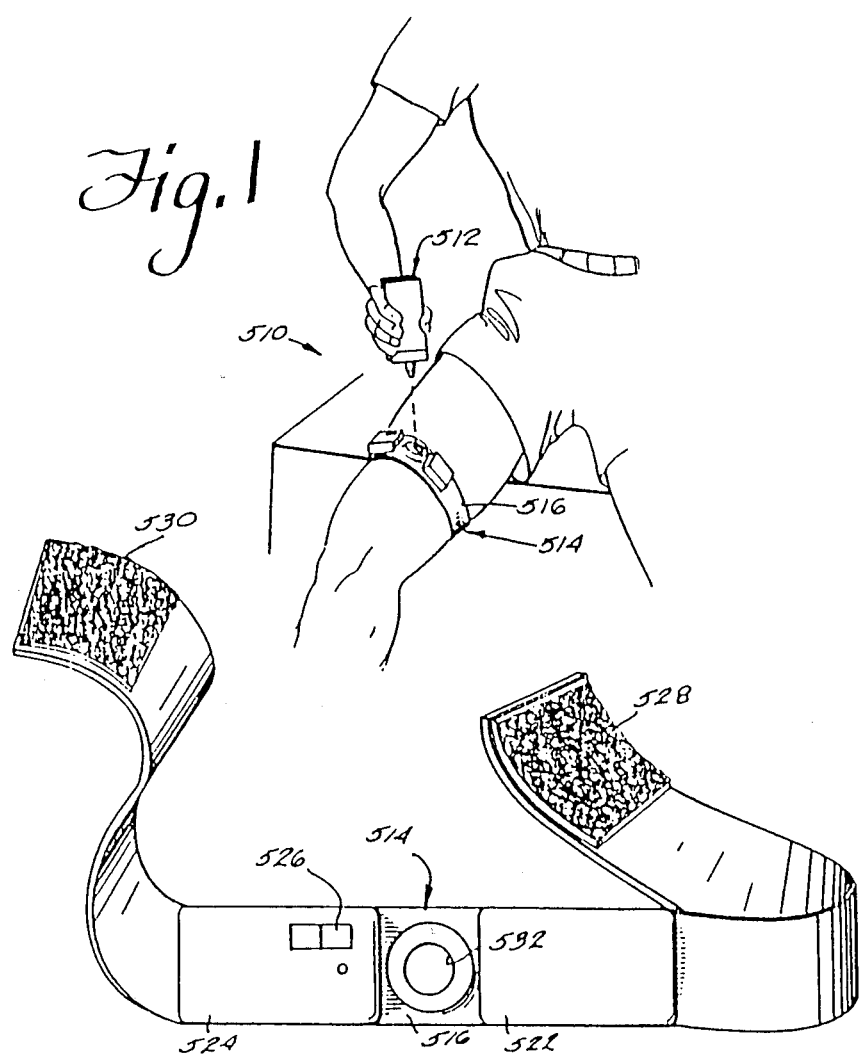
FIG. 1 is a pictorial view illustrating an apparatus embodying the principles of the present invention showing the same in use by a patient.
FIG. 2 is a top plan view of the blood flow enhancing cycle applying assembly shown in FIG. 1.

Referring now more particularly to FIG. 1 there is shown therein an apparatus, generally indicated at 510, which embodies the principles of the present invention. The apparatus 510 as depicted in FIG. 1 includes an automatic injector, generally indicated at 512, of the type disclosed in commonly assigned U.S. Pat. No. 4,658,830. The automatic injector 512 which will be described in detail hereinafter, is generally of the type capable of retaining two medicament ingredients separately, one of liquid and the other a dry powder. The operation of the apparatus is such that the liquid medicament ingredient, which may be a diluent, is mixed with the dry medicament ingredient in response to a first predetermined manual actuating procedure. After the operator insures that a mixture of the ingredients has taken place to form a liquid medicament a second manual actuating procedure is performed which has the effect of moving the hypodermic needle into the muscle tissue of the patient and injecting the liquid medicament into the muscle tissue through the hypodermic needle. This apparatus is considered particularly useful in carrying out the present invention in that it has the capability of containing a significant number of different medicaments in a form capable of small volume storage and yet convertible into a liquid form suitable for injection when it is desired to use the apparatus.

The apparatus 510 further includes an electrical stimulating apparatus, generally indicated at 514, for applying to the patient who is to receive the injection repeated blood flow stimulating cycles. With the apparatus 514 of FIG. 1 it is possible to achieve the period of electrical stimulus during which the muscle tissue tenses by applying the electrical stimulus to the nerves which effect the tension of the muscle tissue rather than to the muscle tissue itself. Indeed, while muscle tension through nerve electrical stimulus is contemplated so also is direct muscular stimulation.

Figure 3:
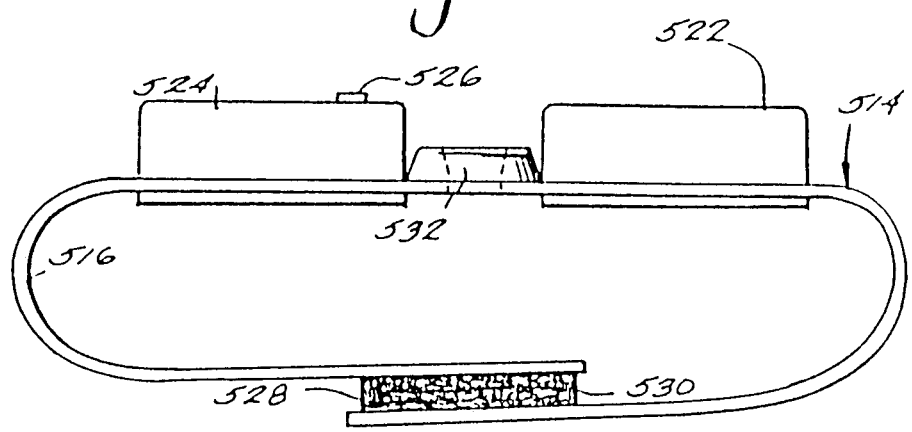
FIG. 3 is a side elevational view of the assembly shown in FIG. 2.
Figure 4:
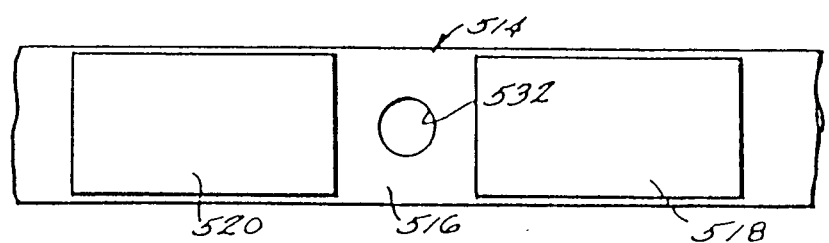
FIG. 4 is a fragmentary bottom plan view of the assembly shown in FIG. 2.

Referring now more particularly to FIGS. 2, 3 and 4, there is shown therein a preferred embodiment of the electrical stimulating apparatus 514. As shown, the apparatus 514 is preferably in the form of an elongated strap 516 which is of generally flexible construction. The strap 516 may be formed of solid plastic or may be of woven material or the like. As best shown in FIGS. 3 and 4, formed on the strap in closely spaced relation on one side thereof there is a pair of electrodes 510 and 520 which may be of any suitable construction. One desirable construction is the provision of a carbon powder loaded vinyl plastic pad. A desirability of this construction is that it may be utilized dry. Nevertheless, it will be understood that conventional wet electrodes may be utilized if desired.

As best shown in FIGS. 2 and 3, fixed to the opposite side of the elongated strap 516 is a pair of housings 522 and 524. Disposed within the housing 522 are batteries. Mounted within the opposite housing 524 is circuitry of the type depicted in FIG. 4 of application Serial No. 735,311 except that a manual actuatable switch 526 is provided for controlling whether or not the blood flow stimulating cycles will be applied to the electrodes.

Mounted on the ends of the strap 516 are Velcro elements 528 and 530. These elements are secured together after the strap has been wrapped around the thigh of the patient, as can be seen in FIG. 1. It will be noted that the strap 516 is provided with target means in the form of a raised opening 532 between the electrode pads 518 and 520 and the housings 522 and 524 for indicating to the operator where the injection should take place to insure that the electrical stimulus will be cooperatively applied.

Referring now more particularly to FIGS. 5 and 6, the apparatus 512 includes an outer housing assembly 612, an inner housing structure 614 mounted within the outer housing assembly for movement forwardly from a storage position into an injecting position. A hypodermic needle assembly 616 is fixed to the forward central portion of the inner housing structure 614 within the outer housing assembly 612 in a sterile condition disposed in a storage position when the inner housing structure 614 is in its storage position and capable of moving outwardly of the outer housing assembly 612 with the inner housing structure 614 for movement into the muscle tissue of a patient when the inner housing structure moves into its injecting position.

Embodied within the inner housing structure 614 is a first medicament container assembly 618 and a side-by-side second medicament container assembly, generally indicated at 620. Operatively associated with the first medicament container assembly 618 and with the inner housing structure 614 is a first stressed spring assembly, generally indicated at 622. A second stressed spring assembly 624 is operatively connected with the second medicament container assembly 620 and with the outer housing assembly 612. As before, a safety cap and releasing assembly, generally indicated at 626, is provided in a storage position for rendering the first and second stressed spring assemblies 622 and 624 incapable of being released. When moved out of its storage position the assembly 626 enables the first stressed spring assembly 622 to be released in response to a first predetermined actuating procedure and then the second stressed spring assembly 624 to be released in response to a second predetermined actuating procedure.

The outer housing assembly 612 includes a main tubular outer housing member 628 having a rear end wall 630 at its rearward end and being open at its forward end. The forward end is closed by a forward housing member 632 which includes a rearwardly extending annular skirt having an interior annular ridge formed therein for engaging within a cooperating annular groove formed in the periphery of the forward end portion of the outer housing member 628. The forward outer housing member 632 also includes a forwardly projecting skin engaging nose portion 634 which is centrally apertured to permit movement of a needle 636 therethrough forming a part of the needle assembly 616.

The inner housing structure 614 includes an inner tubular housing member 638 having an exterior peripheral configuration to slidably engage within the interior peripheral configuration of the outer housing member 628. The inner housing member includes an end wall 640 at its rearward end and, like the outer housing member 628 is open at its forward end. The inner housing structure 614 includes an inner housing member 642 which provides a forward wall having an exterior annular ridge for engaging within an interior peripheral groove formed on the forward end portion of the inner housing member 642. The inner housing member 642 also includes a rearwardly extending portion defining a first container 644 extending rearwardly within the housing member 634 and a second container 646 in side-by-side relation with respect to the first container 644.

It will be noted that the hypodermic needle is of conventional metal configuration having a sharpened forward edge which is engaged within the tip of a resilient sheath 648 so as to close off communication of the hollow interior thereof. The rearward end of the needle communicates with a rearwardly extending passage 650 which is formed in the central forward portion of the inner housing member 642. The rearward end of the passage 650 communicates with the intermediate portion of a cross passage 652, one end of which communicates with the forward end of a passage 654 extending rearwardly in communication with the interior of the first container 644. The first container 644 includes therein a liquid medicament ingredient 656 which is sealingly confined rearwardly by a piston 658 of suitable resilient material so as to be slidably sealingly mounted within the container 644.

The opposite end of the cross passage 652 communicates with a counterbore 660 formed in the forward portion of the member 642. The end of the counterbore 660 is closed by a detachable plug 662. Mounted within the counterbore 660 is a piston valve 664 which, as shown in FIG. 5, is disposed in a storage position closing off communication between the associated end of the cross passage 652 and a short passage 666 extending from the counterbore rearwardly into communication with the second container 646. Mounted within the forward end portion of the second container 646 is a medicament ingredient 668 which preferably is in dry form, specifically a freeze dried powder. The medicament ingredient 668 is sealingly retained within the second container by a piston 670 which is of suitable resilient material like the piston 658 previously described. Mounted in the rearward end portion of the second container 646 in rearwardly spaced relation to the forward piston 670 is a vent piston 672. The vent piston 672 is normally disposed in a storage position spaced inwardly from the rearward end of the second container 646. Formed in the interior periphery of the rearward end portion of the second container 646 is a plurality of annularly spaced vent grooves 674 which extend from the rearward end portion of the piston 672 to the rearward end of the second container 646.

The first stressed spring assembly 622 includes a hollow plunger 676 the forward end o which is flanged, as indicated at 678, and disposed in engagement with the first piston 658 forming a part of the first container 618. The rearward portion of the plunger 676 is slotted, as indicated at 680, to form a plurality of annularly spaced resilient fingers 682 which are integral with the plunger. The fingers 682 are formed with exterior plunger retaining surfaces 684 which face forwardly and outwardly and extend at an angle of approximately 45°. It will be noted that the rearward end wall 640 of the inner housing member 638 is apertured to receive the plunger 676 and is provided with cooperating interior plunger retaining surfaces 686 which face inwardly and rearwardly and extend at an angle of approximately 45°. The fingers 682 of the plunger 676 are also provided with a series of interior plunger releasing surfaces 688. These surfaces are disposed within a common cylindrical plane which has a diameter substantially less than the interior diameter of the hollow piston. The interior plunger releasing surfaces 688 extend from the rearward end of the fingers inwardly a short distance. Mounted within the interior plunger releasing surfaces 688 of the fingers 682 is a first releasing pin 690 which, as shown, forms a part of the safety cap and releasing assembly 626.

It will be understood that when the releasing pin 690 is disposed in engagement with the interior plunger releasing surfaces 688 the associated fingers 682 are prevented from being deflected radially inwardly. The releasing pin 690 thus serves to insure that the exterior plunger retaining surfaces 684 of the fingers 682 will be maintained in engagement with the cooperating plunger retaining surfaces of the inner housing structure 614. This maintenance is provided notwithstanding the bias which is present by virtue of a stressed coil spring 692 forming a part of the spring assembly 622. Coil spring 692 is mounted over the exterior periphery of the plunger 676 with its forward end in engagement with the flange 678 and its rearward end in engagement with the forwardly facing surface of the rearward end wall 640 of the inner housing structure 614. In order to center the coil spring 692, preferably the end wall 640 is provided with an integral forwardly extending cylindrical skirt portion 694 which surrounds the rearward end portion of the coil spring 692.

The second stressed spring assembly 624 is similar to the first in that it includes a hollow plunger 696 having a flange 698 on the forward exterior periphery thereof and slots 700 formed in the rearward end portion thereof so as to define a series of annularly spaced radially inwardly deflectable spring fingers 702. As before, the spring fingers 702 include exterior plunger retaining surfaces 704 and interior plunger releasing surfaces 706. As shown, the rearward end wall 720 of the outer housing member 628 is apertured to receive the second plunger 696 and includes cooperating rearwardly and inwardly facing plunger retaining surfaces 708. In this regard, it will be noted that the end wall 630 is also apertured to allow free movement of the first plunger 676 therethrough. Similarly, the end wall 640 of the inner housing member 638 is apertured to receive a forwardly extending skirt 709 which surrounds the rearward end portion of a stressed coil spring 710, the forward end of which engages the flange 698 and the rearward end of which engages the forward surface of the end wall 630 of the outer housing member 628 surrounded by the skirt 709.

Mounted within the interior plunger releasing surfaces 706 of the fingers 702 of the second plunger 696 is a second releasing pin, generally indicated at 712. The releasing pin 712 is of the type adapted to release the spring fingers 702 either when moved forwardly or rearwardly with respect to the rear end of the associated spring fingers. As shown, the releasing pin 712 includes a forward movement preventing portion 714 which has a diameter sufficient to engage with the interior plunger releasing surfaces 706 so as to be disposed in engagement therewith when the plunger 696 is in its storage position. The releasing pin 712 also includes an actuating button 716 spaced rearwardly from the movement portion 714 and movable forwardly to move the latter out of its storage position into a releasing position or movable rearwardly to remove the movement preventing portion 714 from its storage position. To enable the forward releasing function to take place, the releasing pin 712 includes a movement enabling portion 718 of reduced diameter fixed between the movement preventing portion 714 and the actuating button 716.

In addition to the releasing pins 690 and 712, the assembly 626 also includes a safety key 720 and a safety cap 722 which is formed as an end wall having a manually engagable annular skirt 724 extending forwardly thereof over a substantial portion of the outer housing member 628. The key 720 is in the form of a rearward wall which is integrally connected with the rear end of the pin 690. The key 720 also includes a cylindrical wall portion 726 extending forwardly from the rear wall and a keyed or dual lug shaped wall portion 728 extending forwardly from the portion 726. Formed in the rear wall of the safety cap 722 is a keyed or dual lug shaped opening 730 of a size to receive the keyed portion 728 therethrough which is rotationally aligned therewith. It will be noted however that when the safety key 720 is turned into the storage position shown so as to be rotationally out of alignment, the keyed portion 728 extends between the cap end wall and the outer housing member end wall so as to prevent forward movement of the cap 722 out of its storage position as shown.

The apparatus 512 is assembled by first assembling the first stressed spring assembly 622 in operative relation with the end wall 640 of the inner housing member 638. This is accomplished by moving the plunger 676 rearwardly within the inner housing member 638 until the rearward end of the plunger fingers 682 engage through the opening defined by the plunger retaining surfaces 686. The releasing pin 690 carried by the safety key 720 is then inserted within the fingers 682 to prevent them from moving radially inwardly. In this way the plunger 676 is prevented from moving forwardly by virtue of the interengagement between the plunger retaining surfaces 684 and 686 thus retaining the coil spring 692 in its stressed condition Similarly, the second stressed spring assembly 624 is mounted in operative relation with respect to the outer housing member 628 utilizing releasable pin 712. Next, the safety cap 722 is engaged into its storage position with skirt 724 extending over the outer housing member 628 and with the opening 730 receiving the portion 726 of the key 720. Forward movement of the cap is stopped by the engagement of the keyed portion 728 of the safety key 720 between the cap rear wall and the housing member rear wall.

Next, the containers 644 and 646 are separately filled with the respective medicament ingredients 656 and 668 and sealed by the piston valve 666 and plug 662 at their forward ends and with the pistons 658 and 670-672 at their rearward ends. Next, the housing member 642 defining the two containers is mounted within the inner housing member 638 and needle 636 is mounted in place. After the resilient sheath 648 has been mounted over the needle 636, the entire unit containing the two container assemblies 618 and 620, the inner housing structure 614 and needle assembly 616 is moved rearwardly into the outer tubular housing member 628 and the housing member 632 is snapped over the forward end thereof to complete the assembly.

To operate the apparatus 512 the operator first turns the safety key 720 and moves it rearwardly out of its storage position, as shown in FIG. 17 the removal of the safety key 720 carries with it the safety pin 690 and this movement constitutes the first predetermined actuating procedure which effects the release of the first stressed spring assembly 622. In this regard, it will be noted that the angle of the plunger movement preventing surfaces 684 and 686 are such that as soon as the releasing pin 690 is removed from its storage position, the stress of spring 692 will effect sufficient forward movement of the plunger 676 to cause the spring fingers 682 to be moved radially inwardly until the surface 684 disengages from the surface 686 and then the stressed spring 692 is capable of advancing the plunger 676 forwardly through an operative stroke.

Since the forward flanged end 678 of the plunger 676 is in engagement with piston 658 which in turn is in engagement with the liquid medicament ingredient 656, the force of the released stressed spring 692 serves to increase the pressure within the liquid medicament ingredient 656. This pressure is transmitted to the inner housing member 642 and the liquid within the passage 654 and cross passage 652 therein. The force required to effect movement of the piston valve 664 is considerably less than the force required to effect movement of the entire inner housing member 620 and consequently the piston valve 664 will be moved into a position uncovering the passage 666 so as to allow the pressurized liquid medicament ingredient 656 to pass into the second container 646 to mix with the medicament ingredient 668 therein. As the liquid medicament ingredient 656 flows into the second container 646 piston 670 will be moved rearwardly. This movement in turn causes the air rearwardly of the piston to increase and this increase in pressure in turn builds up until it is sufficient to effect a rearward movement of the vent pistion 672. The vent piston 672 moves rearwardly until it engages the forward flanged end 698 of the plunger 696. In this position vent grooves 674 are communicated with the space within the second container 646 forwardly of the vent piston 672 thus exhausting the pressure to atmosphere and allowing the piston 670 to move freely rearwardly in response to the flow of liquid medicament ingredient 656 from the first container into the second container. When this movement has been completed by virtue of the movement of the piston 658 into its forwardmost position, the operator may at that time shake the apparatus to insure that the liquid medicament 656 will be mixed thoroughly with the medicament ingredient 668 within the second container.

Next, the operator performs the second predetermined manual actuating procedure which has the effect of injecting the liquid medicament formed during the mixing operation. The actuating procedure includes grasping the skirt 724 of the safety cap 722 and moving the nose portion 664 of the outer housing assembly 612 into engagement with the skin of the patient in the area which is to receive the injection, as for example, the thigh. Continued forward movement on the skirt 724 has the effect of effecting the forward movement of the latter with respect to the outer housing assembly 612 during which movement the rear wall of the safety cap 626 will engage the actuating button 712 and move the same forwardly until movement preventing portion 714 thereof is disengaged from the movement preventing surfaces 706 of the spring 710 and the inclination of the surfaces 704 and 708 are such as to cause the plunger 696 to move forwardly deforming the spring fingers 702 radially inwardly until surfaces 704 are disengaged from the surfaces 708. Continued forward movement of the plunger 698 acts through vent piston 672, piston 670 and the liquid medicament forwardly thereof to move the inner housing structure 620 forwardly. During the initial forward movement of the inner housing structure 620, needle 636 pierces through the end of the resilient sheath 648 and extends outwardly beyond the housing nose portion 634 into the muscle tissue of the patient. This outward movement is arrested by the compression of the resilient sheath 648 against the housing portion 634. As soon as the forward movement of the inner housing structure 620 is arrested, continued forward movement of the plunger 696 will result in an outward movement of the liquid medicament forward of the plunger 670 outwardly of the second container through passage 666, cross passage 652, passage 650 and into the hypodermic needle 636 and finally outwardly into the muscle tissue of the patient. This movement of the liquid ingredient from the container 646 into the muscle tissue of the patient continues until the piston 670 reaches its forwardmost position within the container. As soon as this injection procedure has been accomplished, the operator simply removes the device from the patient and in this fashion withdraws the needle from the muscle tissue. The apparatus 512 presents a highly advantageous ability to deliver a maximum amount of medicament. With respect to the medicament capacity advantages of the automatic injecting apparatus 512, it is contemplated that the dry medicament ingredient 668 could include any one or any combination of or preferably all of the following medicament ingredients in a dry form, preferably a freeze dried powder. (1) a clot selective coronary thrombolytic agent, such as t-PA; (2) a blood absorption enhancing agent, such as hydroxylamine hydrochloride; (3) an anti-arrythmic agent, such as lidocaine; (4) a reperfusion damage preventing agent, such as superoxide dismutase of S-aminotrimethyleneaminoethyl thiophosphate, and (5) an anti-reclotting agent. With respect to the anti-reclotting agent, it has been found that to prevent reocclusions or platelet aggregation it is desirable to either 1. inhibit synthesis of thromboxane A (thromboxane $A_2$) with a thromboxane synthetase inhibitor, e.g. an imidazole such as 4-(2[1H-imidazol-1-yl]ethoxy)-benzoic acid hydrochloride (dazoxiben).

2. introduce and antagonist for the receptor of the thromboxane A (thromboxane $A_2$) such as [1α, 2β, (5Z), 3β(1E), 4α]-7-[3-(3-cyclohexyl-3-hydroxy-1-propenyl)-7-oxabicyclo[2.2.1]hept-2-yl]-5-heptenoic acid) (SQ 27,427).

3. introduce another inhibitor of platelet aggregation, e.g. aspirin, indomethacin, naproxin, and sulfinpyrazone.

It will be understood that where combinations of these ingredients are utilized, the ingredients may be separated by dissolvable independent container bags or divider disks. The liquid medicament ingredient 656 is preferably a diluent, such as sterile water. The specific dosages of the medicament ingredients described above can be obtained by reference to commonly assigned U.S. Pat. Nos. 4,658,830, 4,661,469 and 4,656,034.

It will be understood that in using the apparatus 510, the apparatus 514 is first strapped on the patient into position shown in FIG. 1. Next, the automatic injecting apparatus 512 is actuated, as previously indicated, with the final injection function taking place at the target area through the opening 532. After injection has been completed apparatus 512 is withdrawn and switch 526 is turned on for a period sufficient to achieve the desired therapeutic effect, if possible. Since the circuitry of the apparatus 514 is the same as the circuitry 180 previously described its operation will be apparent.

For purposes of background and elaboration of the present disclosure, the disclosures of the patent applications, patents and publications herein mentioned are incorporated by reference into the present specification.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. Apparatus for treating a patient with a liquid medicament for purposes of establishing reperfusion under circumstances where intravenous injection is not practical but the fast response time of an intravenous injection is desirable comprising
   an automatic injector assembly including
   outer housing means,
   medicament cartridge means mounted within said outer housing means in a storage position, said medicament cartridge means including a hypodermic needle, a plurality of medicament containers, and a plurality of medicament ingredients in said medicament containers,
   moving means within said outer housing means for effecting movement of said medicament cartridge means out of said storage position,
   mixing means within said outer housing means operable when said medicament cartridge means is moved out of said storage position for mixing the medicament ingredients to form a liquid medicament,
   said moving means including stressed spring means releasable for effecting movement of said hypodermic needle outwardly of said outer housing means into the muscle tissue of the patient and said mixed liquid medicament outwardly through said needle into the muscle tissue of the patient,
   said mixed liquid medicament including a clot selective coronary thrombolytic agent and a blood absorption enhancing agent.

2. Apparatus as defined in claim 1 wherein said coronary thrombolytic agent is t-PA.

3. Apparatus as defined in claim 2 wherein said liquid medicament includes an anti-arrythmic agent.

4. Apparatus as defined in claim 3 wherein said anti-arrythmic agent is lidocaine.

5. Apparatus as defined in claim 4 wherein said liquid medicament includes an anti-reclotting agent.

6. Apparatus as defined in claim 5 wherein said anti-reclotting agent is a thromboxane synthetase inhibitor.

7. Apparatus as defined in claim 6 wherein said thromboxane synthetase inhibitor is dazoxiben.

8. Apparatus as defined in claim 3 wherein said anti-reclotting agent is an antagonist for the receptor of thromboxane A.

9. Apparatus as defined in claim 8 wherein said antagonist for the receptor of thromboxane A is SQ 27,427.

10. Apparatus as defined in claim 5 wherein said liquid medicament includes a reperfusion damage preventing agent.

11. Apparatus as defined in claim 10 wherein said reperfusion damage preventing agent is superoxide dismutase.

12. Apparatus as defined in claim 10 wherein said reperfusion damage preventing agent is S-aminotrimethyleneaminoethyl thiophosphate.

13. Apparatus as defined in claim 1 wherein said liquid medicament includes an anti-reclotting agent.

14. Apparatus as defined in claim 13 wherein said anti-reclotting agent is a thromboxane synthetase inhibitor.

15. Apparatus as defined in claim 14 wherein said thromboxane synthetase is dazoxiben.

16. Apparatus as defined in claim 13 wherein said anti-reclotting agent is an antagonist for the receptor of thromboxane A.

17. Apparatus as defined in claim 16 wherein said antagonist for the receptor of thromboxane A is SQ 27,427.

18. A device for initiating treatment of a coronary prone individual at a time during the early minutes or hours after the onset of heart attack symptoms, said device comprising
   automatic injector means comprising outer housing means, medicament cartridge assembly means mounted within said housing means in a storage position for movement out of said storage position, cartridge moving means mounted in said housing means for moving said medicament cartridge assembly means out of said storage position,
   said medicament cartridge assembly means including container means, hypodermic needle means, and medicament means disposed in a storage condition within said container means when said medicament cartridge assembly means is in said storage position operable when said medicament cartridge assembly means is moved out of said storage position to provide liquid medicament injectable through said hypodermic needle means,
   said moving means including stressed spring assembly means for moving said hypodermic needle means outwardly of said housing means into the muscle tissue of a patient and said liquid medicament outwardly through said hypodermic needle means into the muscle tissue of a patient,
   said liquid medicament including an agent for preventing platelet aggregation in the blood when absorbed therein from the muscle tissue.

19. A device as defined in claim 18 wherein said liquid medicament includes a blood absorption enhancing agent.

20. A device as defined in claim 19 wherein said liquid medicament includes a clot selective coronary thrombolytic agent.

21. A device as defined in claim 20 wherein said coronary thrombolytic agent is t-PA.

22. A device as defined in claim 21 wherein said liquid medicament also includes an anti-arrythmic agent.

23. A device as defined in claim 22 wherein said anti-arrythmic agent is lidocaine.

24. A device as defined in claim 18 wherein said platelet aggregation preventing agent is a thromboxane synthetase inhibitor.

25. A device as defined in claim 24 wherein said thromboxane synthetase inhibitor is dazoxiben.

26. A device as defined in claim 18 wherein said platelet aggregation preventing agent is an antagonist for the receptor of thromboxane A.

27. A device as defined in claim 26 wherein said antagonist for the receptor of thromboxane A is SQ 27,427.

28. A device as defined in claim 18 wherein said platelet aggregation preventing agent is aspirin, indomethacin, naproxea, or sulfinpyrazone.

29. A device as defined in claim 18 wherein said platelet aggregation preventing agent is aspirin.

30. A device as defined in claim 18 wherein said liquid medicament also includes an anti-arrythmic agent.

31. A device as defined in claim 30 wherein said anti-arrythmic agent is lidocaine.

32. A device as defined in claim 24 wherein said liquid medicament also includes an anti-arrythmic agent.

33. A device as defined in claim 32 wherein said anti-arrythmic agent is lidocaine.

34. A device as defined in claim 26 wherein said liquid medicament also includes an anti-arrythmic agent.

35. A device as defined in claim 34 wherein said anti-arrythmic agent is lidocaine.

36. A device as defined in claim 28 wherein said liquid medicament also includes an anti-arrythmic agent.

37. A device as defined in claim 36 wherein said anti-arrythmic agent is lidocaine.

38. Apparatus for treating a patient with a liquid medicament for purposes of establishing reperfusion under circumstances where intravenous injection is not practical but the fast response time of an intravenous injection is desirable comprising
   an automatic injector assembly including
   outer housing means,
   medicament cartridge means mounted within said outer housing means in a storage position, said medicament cartridge means including a hypodermic needle, a plurality of medicament ingredient containers, a powder medicament ingredient in one of said containers and a diluent ingredient in another of said containers,
   moving means within said outer housing means for effecting movement of said medicament cartridge means out of said storage position,
   mixing means within said outer housing means operable when said medicament cartridge means is moved out of said storage position for mixing the powder and diluent ingredients to form a liquid medicament,
   said moving means including stressed spring means releasable for effecting movement of said hypodermic needle outwardly of said outer housing means into the muscle tissue of the patient and said mixed liquid medicament outwardly through said needle into the muscle tissue of the patient,
   said mixed liquid medicament including a clot selective coronary thrombolytic agent.

39. Apparatus as defined in claim 38 wherein said coronary thrombolytic agent is t-PA.

* * * * *